(12) United States Patent
Scherr (10) Patent No.: US 7,569,013 B2
(45) Date of Patent: Aug. 4, 2009

(54) ENDOSCOPE OPTICS WITH A LATERAL OPTIC-FIBER BUNDLE

(75) Inventor: Patrick Scherr, Schwarzenbek (DE)

(73) Assignee: Olympus Winter & IBE GmbH, Hamburg (DE)

( * ) Notice: Subject to any disclaimer, the term of this patent is extended or adjusted under 35 U.S.C. 154(b) by 863 days.

(21) Appl. No.: 11/121,415

(22) Filed: May 4, 2005

(65) Prior Publication Data

US 2005/0250992 A1 Nov. 10, 2005

(30) Foreign Application Priority Data

May 6, 2004 (DE) .................. 10 2004 023 024

(51) Int. Cl.
*A61B 1/06* (2006.01)
(52) U.S. Cl. .................. 600/160; 600/129; 600/182; 385/117; 362/574
(58) Field of Classification Search .................. 600/101, 600/104, 118, 128–130, 153, 160, 171, 173, 600/175–179, 182; 362/572, 574; 385/117, 385/119
See application file for complete search history.

(56) References Cited

U.S. PATENT DOCUMENTS

| | | | |
|---|---|---|---|
| 3,818,902 A | | 6/1974 | Kinoshita et al. |
| 4,576,147 A | | 3/1986 | Hashiguchi |
| 4,615,333 A | | 10/1986 | Taguchi |
| 4,790,295 A | * | 12/1988 | Tashiro .................. 600/176 |
| 4,846,154 A | | 7/1989 | MacAnally et al. |
| 4,850,342 A | | 7/1989 | Hashiguchi et al. |
| 5,046,816 A | | 9/1991 | Lehmann et al. |
| 5,143,436 A | * | 9/1992 | Baylor et al. .................. 362/582 |
| 5,299,560 A | * | 4/1994 | Hatori .................. 600/121 |
| 5,554,100 A | * | 9/1996 | Leiner et al. .................. 600/182 |

(Continued)

FOREIGN PATENT DOCUMENTS

DE   100 27 477 A1   12/2001

OTHER PUBLICATIONS

Patent Abstracts of Japan, Hard Mirror Objective Optical System, Publication Date: Nov. 28, 1997.

*Primary Examiner*—John P Leubecker
*Assistant Examiner*—Samuel Candler
(74) *Attorney, Agent, or Firm*—Rankin, Hill & Clark LLP (57) ABSTRACT

An endoscope optics receiving a fiber tube to separate optic fibers running between the tubes from an image guide fitted with a distal objective lens, the objective lens being configured to look downward at an oblique angle relative to the axis of the outer tube, the distal end face of the endoscope optics being configured perpendicularly to the line of sight, where a lateral bundle portion of the optic fibers, which is to the side of the fiber tube, terminates at distally bonded fibers substantially parallel to the line of sight, in the end face. The bundle portion is enclosed at its distal end zone by a guide duct. The guide duct is bounded inside by the outside of the fiber tube, outside by the inside of the outer tube, at the bottom by a first chamfer running parallel to the line of sight and being part of a lower external protrusion of the fiber tube touching the outer tube, and at the top by a second chamfer parallel to the line of sight of an internal protrusion of the outer tube touching the fiber tube.

5 Claims, 5 Drawing Sheets

U.S. PATENT DOCUMENTS

| | | | | |
|---|---|---|---|---|
| 5,573,493 A | * | 11/1996 | Sauer et al. | 600/121 |
| 5,584,793 A | * | 12/1996 | Sauer et al. | 600/175 |
| 5,651,759 A | * | 7/1997 | Leiner et al. | 600/182 |
| 5,700,236 A | * | 12/1997 | Sauer et al. | 600/175 |
| 5,718,664 A | | 2/1998 | Peck et al. | |
| 6,152,872 A | * | 11/2000 | Peck et al. | 600/160 |
| 7,160,247 B2 | * | 1/2007 | Deppmeier et al. | 600/129 |

* cited by examiner

Fig. 5

ENDOSCOPE OPTICS WITH A LATERAL OPTIC-FIBER BUNDLE

BACKGROUND OF THE INVENTION

1. Field of the Invention

The present invention relates to the field of endoscope optics.

2. Description of Related Art

Endoscope optic fibers are used to illuminate the field of view. The fibers exhibit a very wide angle of radiation but their beam direction should be central to the field of view as much as possible. Fibers deviating in their directions of radiations entail brightness variations in the field of view. These fibers are bonded in the distal end zone for sealing purposes and to secure their attitudes which were set during assembly.

As regards straight-forward looking endoscope optics (extraneous to the species of the present application), all fibers are mounted parallel to the outer tube axis and terminate in an end face which is perpendicular to said axis. In this design their illuminations are all precisely in the viewing direction—hereafter line of sight.

Construction of optics with oblique lines of sight, wherein the objective lens is downward, is more difficult.

As regards a known endoscope optics of the applicant, which however is extraneous to the species of the present application, all fibers in a fiber bundle are configured above the fiber tube. On account of chamfering downward the inside of the outer tube and by using the same chamfer at the front end zone of the fiber tube, all fibers in the end zone are redirected downward in the direction of the line of sight. However the unilateral configuration of the fiber ends relative to the axis of viewing entails unsatisfactory illumination.

Illumination may be improved using bundle portions mounted on the side of the fiber tube. This design has been made known by STORZ Co. Therein the fiber tube is displaced downward relative to the outer tube. Until far to the rear, the region above the fiber tube and to the side of it is now filled with fibers. Above the fiber tube and starting at the end face, a horizontal wedge is driven into the fibers and it separates a middle, upper bundle portion from two lateral bundle portions, this wedge action forcing said lateral bundle portions downward along the line of sight.

All the above designs require not only aligning the fibers in the line of sight but also that they be mutually parallel. The fibers are configured proximally from the endoscope optics' end zone within a relatively large cross-sectional area between the tubes, said cross-sectional area being required to exceed the total cross-sectional area of the fibers. In this manner it is easier to insert the fibers during assembly. However these fibers also must be compressed in their distal end zones near the end face in order to attain mutual parallelism. This step is implemented in the initially cited design of the applicant by means of the two chamfers at the outer tube and the fiber tube, said chamfers—after the fibers have been installed, and upon advancing the fiber tube distally relative to the outer tube—then constricting the free cross-sectional area between themselves. In the STORZ design, the constriction is implemented by wedge action.

To-date an optimal design solution could not be found in the state of the art. Applicant's known design does in fact allow compressing the fibers well and thus attains good parallelism, but it only does permit this feature within the upper region of the endoscope optics. The STORZ design allows good overall illumination using lateral bundle portions reaching far down, though at less satisfactory compression which is implemented solely by wedging. As a result the fibers are less parallel to each other.

SUMMARY OF THE INVENTION

The objective of the present invention is to create an endoscope optics of the initially cited species offering advantageous light-transmitting lateral bundle portions of which the mutual fiber parallelism has been improved.

In the design of the invention, a lateral bundle portion comprises a guide duct defined in the claim and bounded by the tubes and the two chamfers. One of the chamfers is situated in front of the fiber tube and the other is configured on the outer tube. Accordingly, as the fiber tube is being advanced, the spacing between the chamfers will constrict and thereby the fibers in the guide ducts will be circumferentially compressed and aligned parallel to each other. In this design therefore a lateral bundle portion will be configured precisely in the line of sight while the fibers are aligned in excellent parallelism. The design of the invention implements fiber compression by means of protrusions reliably secured to the two tubes so that elements of the endoscope optics are precluded from detaching: this eventuality arises for instance when using a poorly bonded wedge.

When, as regards the conventional design, the two tubes are axially offset from one another, the guide duct tapers downward. As a result fewer fibers are present in the lower guide duct zone and the illumination of the field of view is then less satisfactory. This drawback is eliminated by the features of the present invention. The fiber tube chamfer in the lower guide duct widens this duct and the centroid of the fibers is shifted downward. While the gap between the tubes is constricted proximally on account of the chamfer, no drawback is incurred thereby because the fibers are incoming obliquely from above from zones of larger cross-sectional area. The chamfer makes it possible to extend the fiber tube distally as far as possible at a large inner cross-sectional area required for the installation of the objective lens at that site.

With the present invention, the endoscope optics comprises two symmetrical, lateral bundle portions, thereby doubling the light output.

Other features of the invention are advantageous. To further increase the light output, a third bundle portion is used which is laterally bounded by the outer tube's internal protrusions which are present anyway. The compression required for the alignment into parallelism is carried out by an upper outer protrusion at the fiber tube.

The upper bundle portion ending with axially parallel fibers in the end face may be made to radiate light in the line of sight by appropriately chamfering the end faces in this region.

BRIEF DESCRIPTION OF THE DRAWINGS

The drawings show an endoscope of the present invention in illustrative and schematic manner.

DETAILED DESCRIPTION OF THE INVENTION

The comparatively complex geometry of the endoscope optics of the invention is shown by a preferred embodiment mode in FIGS. 1 through 5 which are different views of the same optics.

Figure 1:
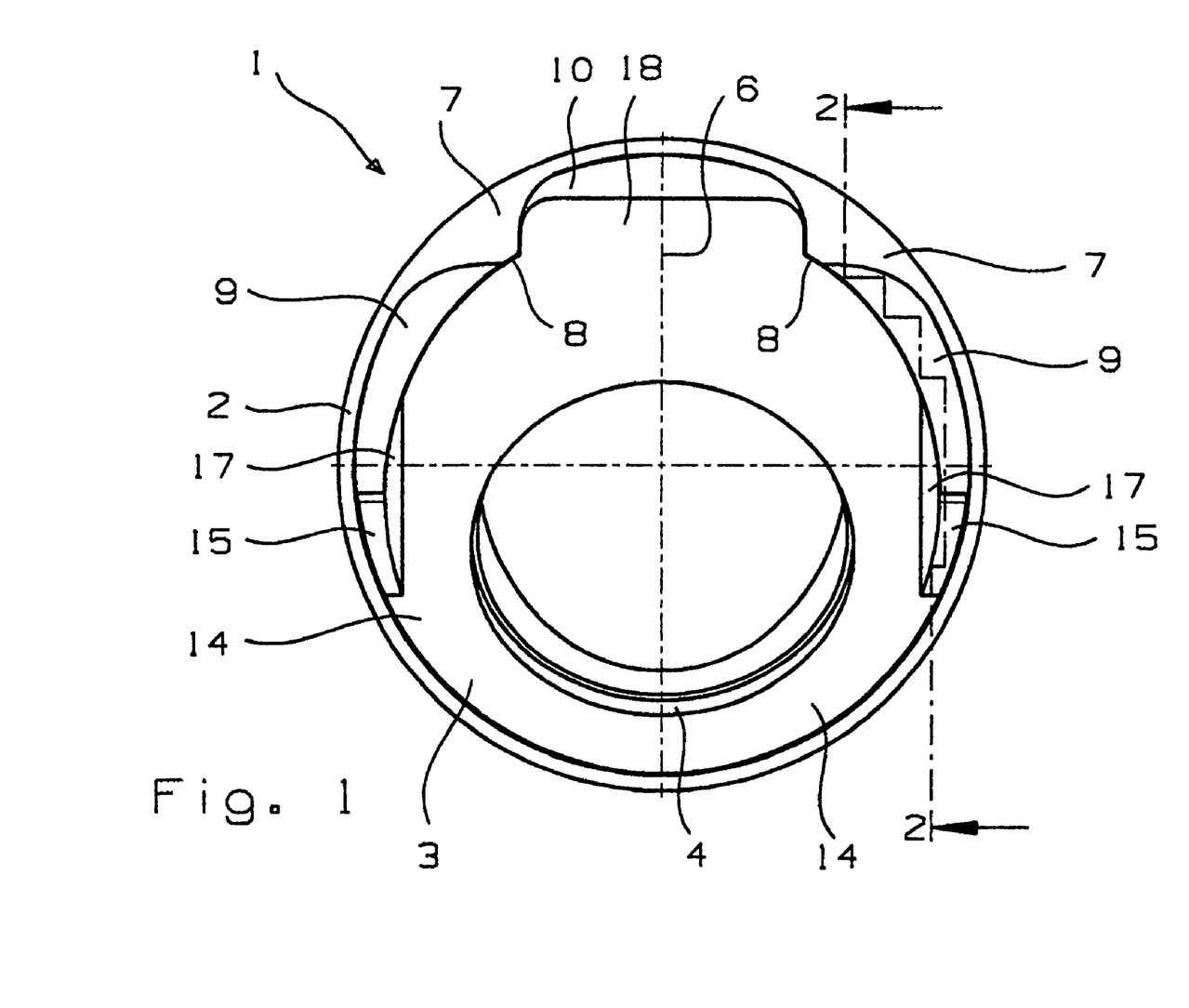
FIG. 1 is a front view of the end face in the axial direction.
Figure 5:
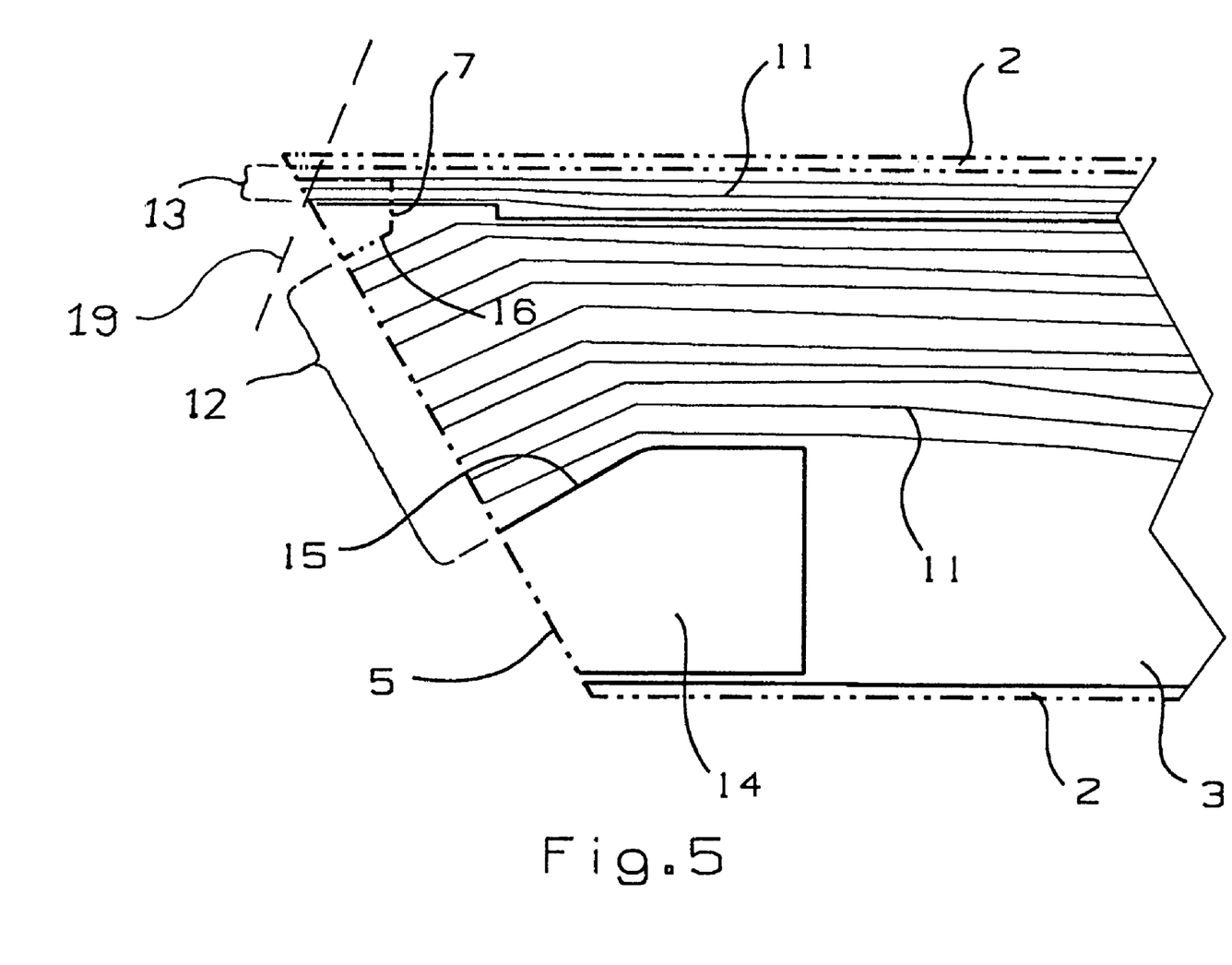
FIG. 5 is the sideview of the fiber tube of FIG. 3 showing the outer tube in dashed lines and diagrammatically indicating the fibers' emplacement.

FIG. 1 is an axial front view of an endoscope optics 1 comprising a outer tube 2 and a fiber tube 3. FIG. 5 shows the outer tube being longitudinally thin-walled; the fiber tube 3 also is longitudinally thin walled but inwardly reinforced at its distal end zone in order to subtend an opening 4 receiving a round window. An omitted optics is mounted inside the fiber tube 3 and looks through the window. An image guide, for instance a configuration of relay lens elements or an optic fiber bundle, also omitted, is situated to the rear. Also a video camera may be mounted behind the objective lens.

Figure 2:
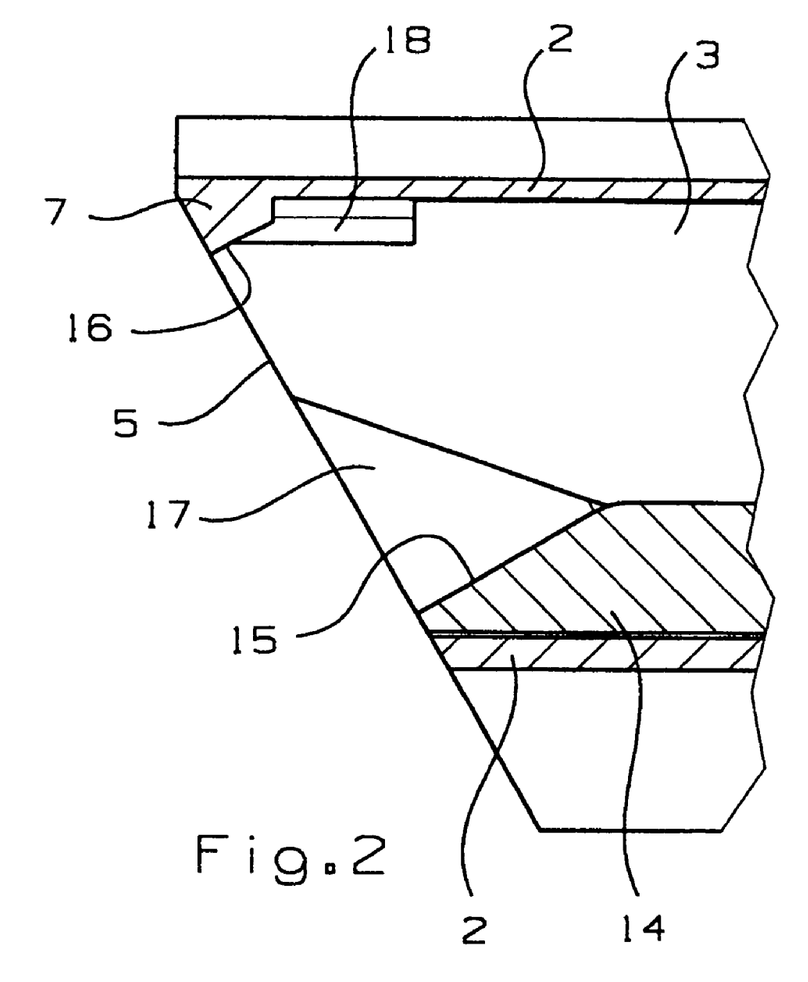
FIG. 2 is a section along the multiple-step sectional line 2-2 of FIG. 1.
Figure 3:
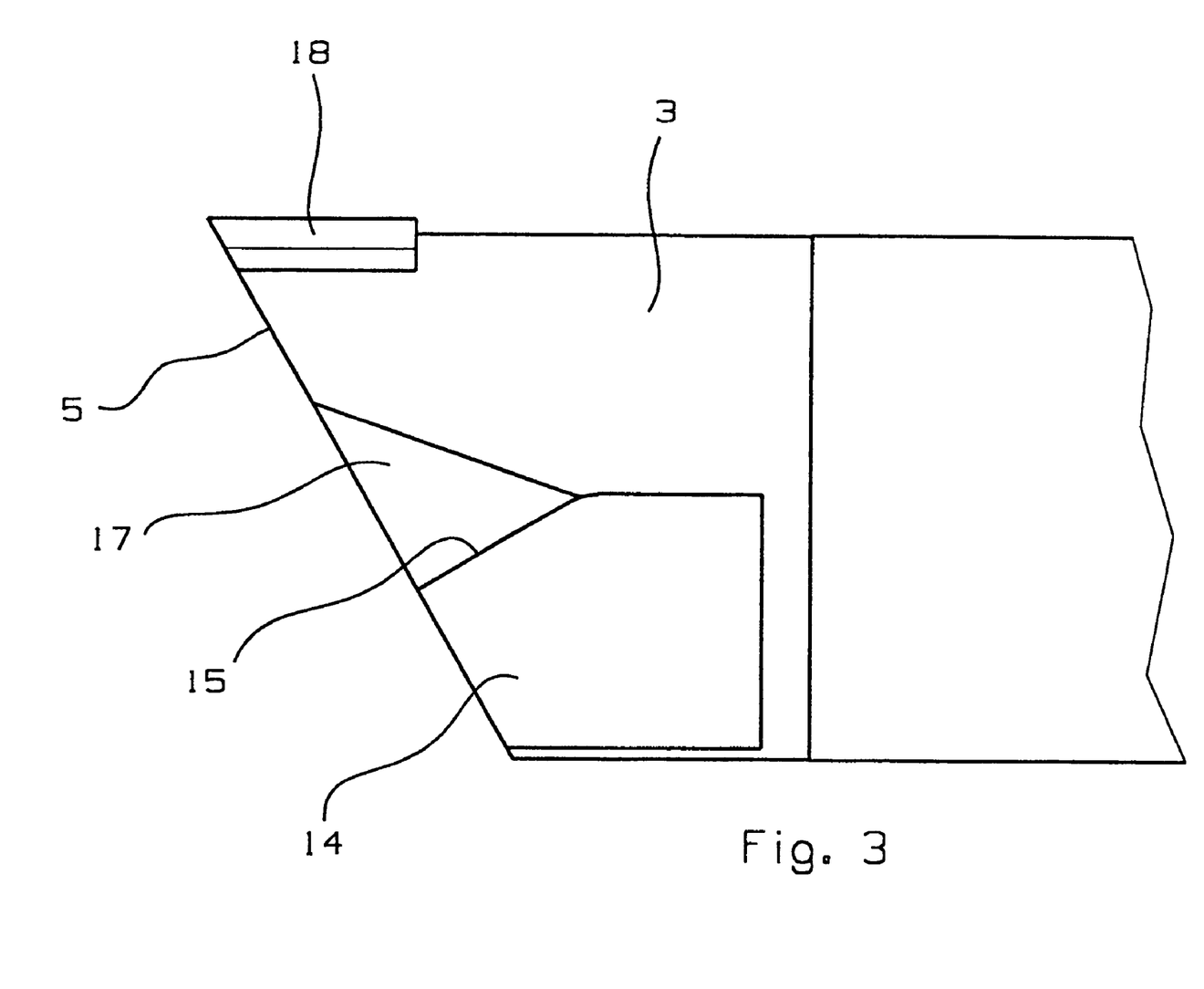
FIG. 3 is a sideview of the fiber tube in the distal end zone.

The sideview of FIG. 2 shows that the endoscope optics' end face 5 runs obliquely to the axis of the outer tube 2. The window aperture 4 is oriented in the plane of the end face 5. The line of sight of the objective lens mounted in the fiber tube 3 is perpendicular to the end face 5 and accordingly this lens—according to FIG. 2—looks obliquely downward relative to the axis of the outer tube 2 at an illustratively angle of 30° but which shall however be selected depending on the endoscope optics' application.

As shown in FIG. 5, the axis of the fiber tube 3 is situated underneath the axis of the outer tube 2 in a manner that the fiber tube by its bottom touches the outer tube 2.

Figure 4:
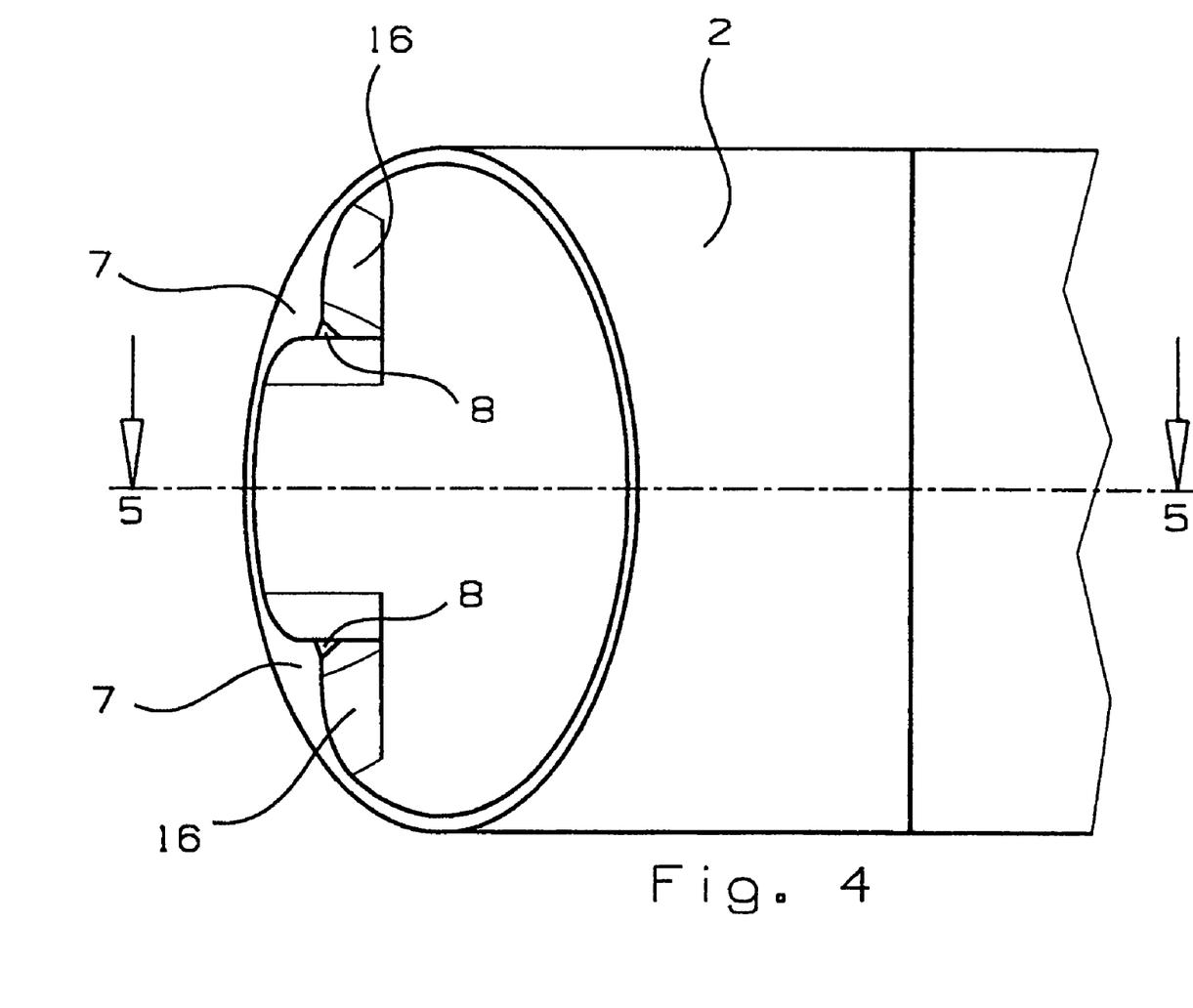
FIG. 4 is a view from below of the distal end zone of the outer tube.

Two inner protrusions 7 are mounted symmetrically to the middle vertical line 6 (FIG. 1) of the endoscope optics in the distal end zone of the outer tube 2, said protrusions each being fitted with a planar tip 8 shown in FIG. 4 and touching the outside surface of the fiber tube 3 as indicated in FIG. 1.

As a result FIG. 1 shows that the gap between the two tubes 2, 3 in the distal end zone as far as the end face 5 is divided into two lateral guide ducts 9 and one upper guide duct 10. FIG. 5 shows optic fibers 11—being received in the gap between the fiber tube 3 and the outer tube 2—that in the form of two lateral bundle portions 12 are situated one each in the lateral guide ducts 9 and in the form of a third, upper bundle portion 13 in the upper guide duct 10.

In its lower zone and on each of its sides, the fiber tube 3 bears an external protrusion 14 which, as shown in FIG. 2, rests against the outer tube 2 and subtends an upward chamfer 15 that, as shown in FIG. 5, is situated in the line of sight, namely perpendicularly to the end face 5. This first chamfer 15 constitutes the lower boundary of the lateral guide duct 9.

The upper boundary of the guide ducts 9 is constituted by second chamfers 16 shown in FIGS. 2, 4 and 5. These second chamfers 16 are subtended by the inner protrusions 7 of the outer tube 2 and, as shown in FIG. 2, are configured parallel to the line of sight, that is parallel to the first chamfers 15. This feature is shown in especially clear manner in the section of FIG. 2 that, because of the somewhat complex section, is laid into FIG. 1. The section of FIG. 2 shows that the chamfers 15 and 16 are parallel to each other and parallel to the line of sight perpendicular to the end face 5.

This feature is also shown in FIG. 5. Therein, optic fibers 11 from the proximal end of the endoscope optics 1 initially are configured in a cross-sectional area between the tubes 2 and 3 which offers them ample space whereby they also might lie in irregular oblique positions and furthermore may cross one another. However they are held in a constricted cross-sectional area in the lateral guide duct 9 and, due to the parallel chamfers 15 and 16, they are compressed into the parallel alignment of FIG. 5 wherein they are precisely mutually parallel and parallel to the line of sight, that is perpendicular to the end face 5.

Assembly of the optic fibers 11 using a lateral bundle portion in one of the lateral guide ducts 9 is made easier in that the fiber tube 9 shall be slightly retracted proximally when the fibers are being pulled inward. In the process and as shown in FIGS. 2 and 5, the spacing between the chamfers 15 and 16 is enlarged and therefore the lateral fiber bundles 12 now may be pulled inward in problem-free manner. Thereupon the fiber tube is pushed forward into the assembly position indicated in FIGS. 2 and 5, as a result of which the cross-sectional area of the lateral guide ducts 9 is constricted by the mutual approach of the chamfers 15 and 16, namely circumferentially. Beforehand, namely in the distal end zone and therefore inside the guide ducts, the fibers were impregnated with adhesive, and thereafter they are made mutually parallel by this constriction procedure, whereupon, at the end of adhesive curing, they will be cut off at the end face 5, for instance by grinding.

As shown by FIG. 1, the gap between the fiber tube 3 and the outer tube 2 in the lateral guide duct 9 decreases from top to bottom on account of the downward axially offset position of the fiber tube 3 relative to the outer tube 2. As a result, absent other design features, a larger cross-sectional area would be available in the upper than in the lower zone.

To prevent such a consequence, chamfered surfaces 17 are provided in each lateral guide duct 9 in its lower zone and run distally inward in such oblique manner that in this zone the gap between the tubes is flaring toward the end face 5.

As a result and as shown in FIG. 1, the cross-sectional area of the lateral guide duct 9 will be enlarged in the lower zone of the end face 5. On the other hand the gap between the tubes 2, 3 is proximally constricted because of the oblique position of the surfaces 17. Nevertheless the emplacement of the fibers 11 remains undisturbed because, as indicated in FIG. 5, they run from above from a region of larger separation to enter between the tubes.

As shown by FIG. 5, the upper guide duct 10 receives fibers 11 running parallel to the axis of the outer tube 2. These fibers are held in place in the region of the guide duct 10 by an upper external protrusion 18 of the fiber tube 3 (FIGS. 1, 2 and 3), said protrusion acting between the inner protrusions 7 of the outer tube 2.

If the fibers 11 of the upper bundle portion 13 were to terminate in the end face 5, then the fibers' end surfaces situated in the end faces 5 would be configured at a disadvantageous angle. Due to light refraction between the different media, namely glass and air or glass and water (depending on where the endoscope optics is used), an upward deviation from the axis of the outer tube 2 would ensue, that is, away from the line of sight. Therefore, In preferred manner, as regards the region of the upper bundle portion 13, that is of the upper guide duct 10, a section of the end face 5 should subtend another angle, for instance along line 19 in FIG. 5. In that case and on account of light refraction at the end surfaces of the optic fibers 11, the light is radiated parallel to the line of sight, namely perpendicularly to the end face 5.

The invention claimed is:

1. An endoscope optics (1) comprising:
 a fiber tube (3) and an outer tube (2) receiving a fiber tube (3)
 the fiber tube (3) receiving an image guide and separating it from optic fibers (11) arranged between the tubes (2, 3)
 the image guide comprising a distal objective lens being configured to look downward with its line of sight at an oblique angle relative to an axis of the outer tube (2), the distal end face (5) of the endoscope optics (1) being configured perpendicularly to the line of sight, the optic fibers (11) comprising a lateral bundle portion (12) terminating in the end face (5) on a side of the fiber tube (3), the distal end portion of the fibers of the lateral bundle portion (12) being bonded and being aligned substantially parallel to the line of sight, wherein the bundle portion (12) is enclosed at its distal end portion by a guide duct (9) which is bounded at its inside by the outside of the fiber tube (3), at its outside by the inside of the outer tube (2), at its bottom by a first chamfer (15) running parallel to the line of sight and being part of a lower external protrusion (14) of the fiber tube (3), said external protrusion (14) touching the outer tube (2), and at its top by a second chamfer (16) running parallel to the line of sight and being part of an internal protrusion (7) of the outer tube (2), said internal protrusion (7) touching the fiber tube (3).

2. The endoscope optics as claimed in claim 1, wherein an axis of the fiber tube (3) runs below the axis of the outer tube (2), wherein a gap between the fiber tube (3) and the outer tube (2) in a lower region of the lateral guide duct (9) increases toward the end face (5) by means of a beveled surface (17) on the outer surface of the fiber tube (3).

3. The endoscope optics as claimed in claim 1, wherein two lateral bundle portions (12) are mounted in identical guide ducts (9), which are configured symmetrically on each side of the fiber tube (3).

4. The endoscope optics as claimed in claim 3, wherein an upper bundle portion (13) in which the fibers run parallel to the axis of the outer tube (2) is configured between the bundle portions (12) in an upper guide duct (10), which is bounded by axially parallel walls constituted by the inside of the outer tube (2), by an upper external protrusion (18) of the fiber tube (3), and by the internal protrusion (7) of the outer tube (2).

5. The endoscope optics as claimed in claim 4, wherein the end face (5) is chamfered in a region of the upper bundle portion (13) at another angle (19) such that the light of the fibers (11) is refracted from its end surfaces into the line of sight.

* * * * *

UNITED STATES PATENT AND TRADEMARK OFFICE
CERTIFICATE OF CORRECTION

PATENT NO. : 7,569,013 B2
APPLICATION NO. : 11/121415
DATED : August 4, 2009
INVENTOR(S) : Scherr

Page 1 of 1

It is certified that error appears in the above-identified patent and that said Letters Patent is hereby corrected as shown below:

On Title Page, in Section [57] Abstract, after "An endoscope optics", insert -- having an outer tube --

Signed and Sealed this

Tenth Day of November, 2009

David J. Kappos
*Director of the United States Patent and Trademark Office*